Aug. 11, 1942. G. D. BUSH Plant Pat. 538
DOUBLE MOCK ORANGE
Filed Oct. 27, 1941
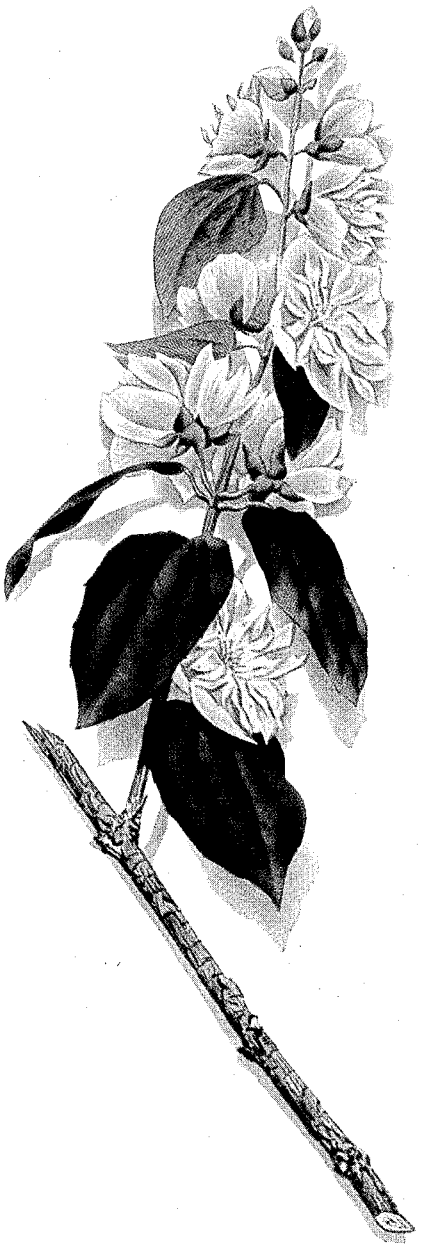
Inventor
Guy Duane Bush
By Williamson & Williamson
Attorneys Patented Aug. 11, 1942

Plant Pat. 538

UNITED STATES PATENT OFFICE

538

DOUBLE MOCK ORANGE

Guy Duane Bush, Minneapolis, Minn.

Application October 27, 1941, Serial No. 416,664

1 Claim. (Cl. 47—69)

The present invention relates to a new double flowering variety of mock orange technically known as Philadelphus.

The mother shrub was developed as a seedling from the *Philadelphus virginalis* and is located at Minneapolis, Minnesota. I have asexually reproduced young shrubs from the original mother shrub.

In the accompanying original drawing wherein my new variety of shrub is typically illustrated in color there is shown a cluster of flowers, leaves, flower branch and stem shooting from one of the old and main canes of the shrub.

Of the various types of mock orange or Philadelphus my new variety is most similar to the *Philadelphus virginalis*. It is distinguished from the *virginalis* chiefly in the following respects. All of the flowers of my new variety are true double flowers or what may be spoken of as extra double flowers, while in the *virginalis* many of the flowers are not double and the double flowers of the *virginalis* are not as heavily plumed or as thick as my new variety. The flowers are not quite as deep or cupped as the *virginalis* opening out flatter than the *virginalis*. The stamens nearly all develop into narrow curly petals giving the bloom a much more double effect than the *virginalis* and the flower thus appears whiter than the *virginalis* inasmuch as there is less orange yellow at the center of the blossom than is found in the *virginalis*. The flower is exceptionally sweet scented and has much of the appearance of a double white delphinium, the center of the petals being finer than in the *virginalis*. The leaf is somewhat larger than the *virginalis* being considerably wider. The leaf also is somewhat brighter and of a lighter colored green than the *virginalis*. The leaves hang on the canes with more of a droop and slightly curved downwardly and inwardly than the *virginalis* and in marked contract with the *Philadelphus grandiflora* which has leaves that curl upwardly showing the underside of the leaf. The shrub, therefore, has a neater, more uniform color and more pleasing appearance than some other varieties such as the *grandiflora*. The flower branches are somewhat grayer than the *virginalis* while the new shoots are somewhat greener than the *virginalis*.

In addition to being characterized by its unusual double flowers my new variety is characterized by its fast growth and hardiness. It grows considerably larger than the *virginalis* and much more vigorously and rapidly. It is easily propagated and it won't freeze back or winter kill readily. It is much more resistant to winter weather than is the *virginalis*. The mother shrub as well as the young stock up to the present time have never shown signs of winter injury or freezing back in the Minnesota climate.

For convenient summary the following detailed description of this new variety of mock orange is given:

Shrub:
- Large.
- Vigorous.
- Upright.
- Tall.
- Vase formed.
- Rapid growing.
- Exceptionally hardy.
- Very productive.
- Regularly flowering.
- Highly resistant to Minnesota climate.

Old canes:
- Slender.
- Gray—grayer than *virginalis*.
- Bark lightly furrowed and slightly peeling.

Lateral flowering branches or stems—after first year's growth:
- 4 to 10 inches long.
- Straight and slender.
- Greenish lemon yellow.

New canes—under one year old:
- Do not have flowers during the first year's growth.
- Leaves are large and luxurious—larger than on old canes.

Leaves:
- 1'' to 3½'' long averaging 2'' slightly larger than *Philadelphus virginalis*.
- ¾'' to 2½'' wide at widest point averaging about 1½'', wider than *virginalis*.
- *Color*.—green, lighter and brighter than *virginalis*—bottom whitish green.
- Ovate acuminate—some slightly broader taper pointed.
- Thin.
- Slightly rugose pubescent on back side, surface smooth but veined.
- On new canes are slightly lighter green than on lateral branches running from 2½'' to 4½'' long and 1¼'' to 3'' wide. Particularly on new canes and also to a less noticeable extent on lateral branches the leaves have a uniform drooping habit and curve downwardly and inwardly somewhat preventing exposure of the undersides of the leaves and giving the shrub a neat uniformly colored appearance.

Margin:
Slightly toothed or serrated.
Peduncle:
Short.
Slender.
Color same as leaf.
Flowers:
Date of bloom in Minnesota about mid June depending on weather conditions—about the same as *virginalis*.
Best blooms slightly larger than silver dollar.
Blooms in clusters of 2 to 7.
Outer petals more saucer shaped than cup shaped—narrower and more open than *virginalis*.
Stamens have nearly all developed into narrow curly petals giving the bloom a more intensely double effect than in *virginalis* hence less orange yellow at center. Each bloom is double.
Anthers of stamens are orange yellow, filament white, pistils greenish white later turning green.
Pure white flower.
Center of flower resembles double white delphinium.
Sweet scented.
Sepals of calyx:
Star shape—usually 4 pointed but sometimes 5 or 6 pointed—occasionally 7 pointed.
Ovary is bulging.
Buds are generally similar to *virginalis*.

The flowers above described and the shrubs producing the same will vary in slight detail depending on the climatic conditions under which they are grown. Propagated cuttings from the mother tree have produced flowers during their second year's growth.

What is claimed is:

A mock orange variety substantially as herein shown and described, characterized by the extra double character of all its flowers, the sweet scent of its flowers, its fast growing quality, its vigor and hardiness, its ability to withstand winter killing and its ease in propagation.

GUY DUANE BUSH.